United States Patent
Jang et al.

(10) Patent No.: US 11,992,562 B2
(45) Date of Patent: May 28, 2024

(54) PERCUTANEOUS ABSORPTION PREPARATION FOR TREATING DEMENTIA COMPRISING DONEPEZIL

(71) Applicants: DONG-A ST CO., LTD., Seoul (KR); KM TRANSDERM LTD., Osaka (JP)

(72) Inventors: Sun-Woo Jang, Seoul (KR); Chang-Yell Shin, Seoul (KR); Jeong-Soo Kim, Yongin-si (KR); Hae-Sun Kim, Seongnam-si (KR); Kwang-Ho Cha, Seoul (KR); Hyun-Jung Kim, Yongin-si (KR); Masaoki Goto, Osaka (JP)

(73) Assignees: DONG-A ST CO., LTD., Seoul (KR); KM TRANSDERM LTD., Osaka (JP)

( * ) Notice: Subject to any disclaimer, the term of this patent is extended or adjusted under 35 U.S.C. 154(b) by 473 days.

(21) Appl. No.: 16/957,774

(22) PCT Filed: Nov. 7, 2018

(86) PCT No.: PCT/KR2018/013439
§ 371 (c)(1),
(2) Date: Jun. 25, 2020

(87) PCT Pub. No.: WO2019/132229
PCT Pub. Date: Jul. 4, 2019

(65) Prior Publication Data
US 2021/0059956 A1 Mar. 4, 2021

(30) Foreign Application Priority Data
Dec. 27, 2017 (KR) .................. 10-2017-0180647

(51) Int. Cl.
| | | |
|---|---|---|
| A61K 9/70 | (2006.01) |
| A61F 13/02 | (2006.01) |
| A61K 31/445 | (2006.01) |
| A61K 47/12 | (2006.01) |
| A61K 47/14 | (2017.01) |
| A61K 47/32 | (2006.01) |
| A61K 47/44 | (2017.01) |
| B29D 7/01 | (2006.01) |
| B29K 71/00 | (2006.01) |
| B29L 31/00 | (2006.01) |

(52) U.S. Cl.
CPC ........ *A61K 9/7084* (2013.01); *A61F 13/0276* (2013.01); *A61K 31/445* (2013.01); *A61K 47/12* (2013.01); *A61K 47/14* (2013.01); *A61K 47/32* (2013.01); *A61K 47/44* (2013.01); *A61F 2013/0296* (2013.01); *B29D 7/01* (2013.01); *B29K 2071/02* (2013.01); *B29L 2031/753* (2013.01)

(58) Field of Classification Search
CPC ...... A61K 31/445; A61K 47/12; A61K 47/14; A61K 47/32; A61K 47/44; A61K 9/7053; A61K 9/7084; B29D 7/01; B29K 2071/02; B29L 2031/753; A61F 13/0276; A61F 2013/0296; A61P 25/28
See application file for complete search history.

(56) References Cited

U.S. PATENT DOCUMENTS

| | | | | |
|---|---|---|---|---|
| 2003/0027841 A1* | 2/2003 | Murahashi | ............. | A61P 25/28 514/319 |
| 2014/0308335 A1* | 10/2014 | Hamada | ................ | A61K 31/44 424/443 |
| 2017/0290780 A1* | 10/2017 | Choi | ..................... | A61K 47/30 |

FOREIGN PATENT DOCUMENTS

| | | | | |
|---|---|---|---|---|
| EP | 2491931 B1 * | 9/2017 | | A61K 31/445 |
| JP | 11-315016 A | 11/1999 | | |
| KR | 10-2005-0037405 A | 4/2005 | | |
| KR | 10-2009-0101667 A | 9/2009 | | |
| KR | 10-2012-0093293 A | 8/2012 | | |
| KR | 10-2016-0074433 A | 6/2016 | | |
| KR | 10-2016-0120778 A | 10/2016 | | |
| WO | 2011049038 A1 | 4/2011 | | |

OTHER PUBLICATIONS

International Search Report of PCT/KR2018/013439 dated May 15, 2019 [PCT/ISA/210].

* cited by examiner

*Primary Examiner* — Kara R McMillian
(74) *Attorney, Agent, or Firm* — Sughrue Mion, PLLC

(57) ABSTRACT

A percutaneous absorption preparation is disclosed. The percutaneous absorption preparation contains donepezil for treatment of dementia, wherein the preparation includes: (a) donepezil or its pharmaceutically acceptable salt as active component, (b) propylene glycol monocaprylate as solubilizer, and (c) styrene-isoprene-styrene block copolymer ("SIS") as adhesive. The percutaneous absorption preparation has low skin irritation and high skin penetration.

7 Claims, 8 Drawing Sheets
(2 of 8 Drawing Sheet(s) Filed in Color)

[Fig. 8]
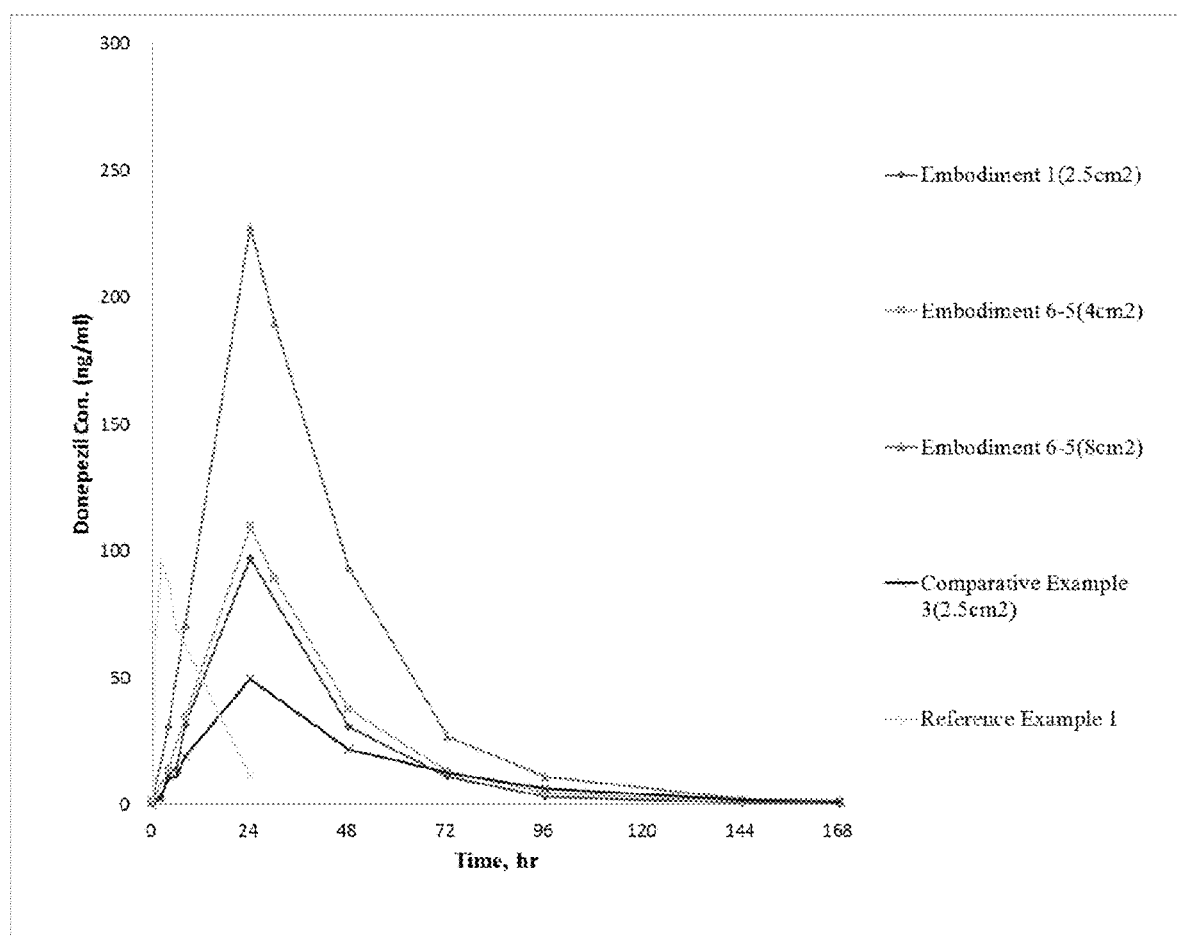

PERCUTANEOUS ABSORPTION PREPARATION FOR TREATING DEMENTIA COMPRISING DONEPEZIL

CROSS REFERENCE TO RELATED APPLICATIONS

This application is a National Stage of International Application No. PCT/KR2018/013439, filed Nov. 7, 2018, claiming priority to Korean Patent Application No. 10-2017-0180647, filed Dec. 27, 2017.

TECHNICAL FIELD

The present invention relates to the percutaneous absorption preparation for treating dementia comprising donepezil with an excellent degree of skin penetration and, simultaneously, great physicochemical stability and hypoallergenic characteristics.

BACKGROUND ART

Alzheimer's dementia, a degenerative disease, is a syndrome characterized by the combined cognitive impairment characterized by memory loss, impaired judgment, behavior disorder and such. Though the cause of dementia has not been fully elucidated, it is known that levels of acetylcholine-synthesizing choline acetyltransferase and neurotransmitter acetylcholine in brains of dementia patients are decreased 20~30% and 16~30%, respectively, compared to non-patients. Hence, it is known that increasing the level of acetylcholine in brain can improve the cognitive ability of dementia patients.

Meanwhile, donepezil, an acetylcholinesterase inhibitor, is a drug developed to treat Alzheimer's dementia and a typical product on the market containing donepezil is an oral preparation called Aricept®. However, administration of donepezil as an oral preparation causes severe side effects such as nausea, vomiting, diarrhea and such due to sudden increase in blood concentration and problems of administration convenience to elderly patients with decreased ability to swallow.

Because of these problems, various studies relating to the percutaneous absorption preparation for treating dementia comprising donepezil or its salts were internationally conducted. But there is no percutaneous absorption preparation comprising donepezil on the market yet due to its problems of 1) low degree of skin penetration, 2) skin irritation and 3) low physicochemical stability due to crystal precipitation.

In other words, because of the low degree of skin penetration of the percutaneous absorption preparation comprising donepezil, in order to deliver sufficient amount of drug through the skin, the size of the percutaneous absorption preparation adversely increase. Furthermore, increasing the drug level or using large quantity of penetration enhancers to improve the level of skin penetration adversely induces the crystal precipitation and skin irritation.

Studies to overcome the low degree of skin penetration of the percutaneous absorption preparation comprising donepezil are disclosed in various prior arts including Republic of Korea Patent No. 1454362, Republic of Korea Patent Application No. 2016-0074433, Republic of Korea Patent No. 1485822, Republic of Korea Patent No. 1325104, Republic of Korea Patent No. 1239150, Republic of Korea Patent Application No. 2012-0093293, United States Patent Application Publication No. 2013-0224262, United States Patent Application Publication No. 2010-0080842.

For example, Republic of Korea Patent No. 1454362 discloses the percutaneous absorption preparation comprising donepezil, as the active component, EVA adhesive (main component: polyethylene vinyl acetate copolymer), pyrrolidone derivatives, as a skin penetration enhancer (solubilizer), $C_{8-18}$ aliphatic derivatives including propylene glycol monocaprylate, and triacetin. Republic of Korea Patent Application No. 2012-0093293 discloses the percutaneous absorption preparation comprising donepezil as the active component, styrene-isoprene-styrene block copolymer as a base polymer for adhesive, lauryl alcohol as a skin penetration enhancer (solubilizer), lauromacrogol, and triacetin.

However, though Republic of Korea Patent No. 1454362 discloses EVA adhesive including rosin ester resin to prevent precipitation of donepezil, the maximum level of skin penetration in human cadaver skin is 7.74 ug/cm$^2$/hr, which is inadequate. Republic of Korea Patent Application No. 2012-0093293 also discloses hydrogenated rosin glycerin ester to inhibit precipitation of donepezil, but its composition also induces moderate irritation when large quantity of rosin ester resin is used.

The rosin ester resins are typically mixed to increase adhesiveness in the percutaneous absorption preparation. As they are also used in the studies relating to the percutaneous absorption preparation comprising donepezil as solubilizers (absorption enhancers or skin penetration enhancers) to promote the skin penetration, as in the above prior arts, the rosin ester resins are used in large quantities to inhibit the crystal precipitation of donepezil by increasing its solubility. However, when they are used in large quantities, they adversely increase the skin irritation.

Therefore, the present inventors conducted studies related to the percutaneous absorption preparation comprising donepezil, and by evaluating solubility test and skin penetration test of various solubilizers (absorption enhancers or skin penetration enhancers) they surprisingly found that when propylene glycol monocaprylate is used, a percutaneous absorption preparation without donepezil crystal precipitation and with high degree of skin penetration at the same time can be made without additionally mixing the rosin ester resins. They also surprisingly found that high degree of skin penetration can only be achieved by mixing the above propylene glycol monocaprylate with a styrene-isoprene-styrene block copolymer (hereinafter "SIS") among various base polymers for adhesive and completed the present invention.

DISCLOSURE

Technical Problem

The present invention provides the percutaneous absorption preparation comprising donepezil without the problematic drug crystal precipitation and skin irritation but at the same time with the high degree of skin penetration.

Technical Solution

The present invention relates to the percutaneous absorption preparation for treating dementia comprising donepezil comprised of a backing layer, drug-containing layer, and release liner, wherein the drug-containing layer comprises (a) donepezil or its pharmaceutically acceptable salt as the active component, (b) propylene glycol monocaprylate as the solubilizer, and (c) styrene-isoprene-styrene block copolymer ("SIS") as adhesive.

The present invention is specifically described as follows.

The above donepezil used in the present invention is acetylcholinesterase inhibitor and it is useful to use donepezil or its pharmaceutically acceptable salts in its free base form. Acid addition salts formed by pharmaceutically acceptable free acids are useful as the above pharmaceutically acceptable salts. The acid addition salts are obtained from mineral acids such as hydrochloric acid, nitric acid, phosphoric acid, sulfuric acid, hydrobromic acid, hydroiodic acid, nitrous acid, or phosphorous acid and non-toxic organic acids such as aliphatic mono- and dicarboxylate, phenyl-substituted alkanoate, hydroxyalkanoate and alkanedioate, aromatic acids, aliphatic and aromatic sulfonic acids. In such salts are the pharmaceutically non-toxic salts such as sulfate, pyrosulfate, bisulfate, sulfite, bisulfite, nitrate, phosphate, mono-hydrogen phosphate, dihydrogen phosphate, meta-phosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzenesulfonate, xylene sulfonate, phenylacetate, phenyl propionate, phenyl butyrate, citrate, lactate, β-hydroxybutyrate, glycolate, maleate, tartrate, methanesulfonic acid, propanesulfonate, naphthalene-1-sulfonate, naphthalene-2-sulfonate, or mandelate, but is not limited thereto.

From the aspects of dispersibility and transdermal absorbability, in the drug-containing layer of the present invention, free base donepezil is preferably used. While the content of donepezil in the patch is not particularly limited, it is preferably 1 wt %-20 wt %, more preferably 1.5 wt %-15 wt %, most preferably 2 wt %-10 wt %, of the drug-containing layer, in consideration of dispersibility in the drug-containing layer and transdermal absorbability.

The propylene glycol monocaprylate of the present invention is used as the solubilizer and, considering the pattern of drug crystal precipitation and degree of skin penetration, mix proportion of donepezil:propylene glycol monocaprylate is 1:0.75-1:4.5 by weight, preferably 1:1.5-1:4.5 by weight, and more preferably 1:1.5-1:3 by weight. The degree of skin penetration of donepezil decreases as the amount of the solubilizer, propylene glycol monocaprylate, decreases, but when the mix proportion of donepezil, propylene glycol monocaprylate is below 1:0.75 by weight, the donepezil crystal precipitates form thereby decreasing the degree of skin penetration.

While the content of propylene glycol monocaprylate in the percutaneous absorption preparation of the present invention is not particularly limited, it is preferably 1 wt %-40 wt %, more preferably 3 wt %-30 wt %, most preferably 5 wt %-25 wt %, of the drug-containing layer, in consideration of dispersibility of donepezil in the drug-containing layer and transdermal absorbability of donepezil.

Styrene-isoprene-styrene block copolymer is used as adhesive in the present invention. Styrene-isoprene-styrene block copolymer is a thermoplastic elastomer composed of styrene and isoprene. Various properties such as melting point and solution viscosity vary depending on styrene content and diblock content in the styrene-isoprene-styrene block copolymer.

The styrene-isoprene-styrene block copolymer used in the present invention is not particularly limited, but it is 0.5 Pa*s or more, more preferably 0.7 Pa*s or more, particularly preferably 0.9 Pa*s or more when the solution viscosity of the styrene-isoprene-styrene block copolymer is measured. The upper limit of the solution viscosity is not particularly limited, but it is preferably 2.0 Pa*s or less, more preferably 1.8 Pa*s or less. As used herein, the "solution viscosity" is a value measured based on "method for measuring the viscosity of styrene-isoprene-styrene block copolymer" described in the Japanese Pharmaceutical Excipients 2013" (published by YAKUJI NIPPO LIMITED).

Specifically, the following commercially available styrene-isoprene-styrene block copolymer can be used. Examples of such commercially available product include "KRATON D1111", "KRATON D1163", "KRATON D1113" and "KRATON D1119" manufactured by KRATON POLYMERS, "JSR SIS5002", "JSR SIS5229", "JSR SIS5403" and "JSR SIS5505" manufactured by JSR Corporation, "Quintac 3421", "Quintac 3433N", "Quintac 3520", "Quintac 3450", "Quintac 3270" manufactured by Zeon Corporation and the like. Of these, "KRATON D1163", "KRATON D1113", "JSR SIS5403", "JSR SIS5505", "Quintac 3433N", "Quintac 3520" are preferably used, and "JSR SIS5505", "Quintac 3520" are particularly preferably used.

When the content of styrene-isoprene-styrene block copolymer in the drug-containing layer is too small, the shape of the drug-containing layer is difficult to maintain, and when the content is too high, skin permeability tends to be lower. Therefore, the content of the styrene-isoprene-styrene block copolymer in the drug-containing layer of the present invention is preferably not less than 10 wt %, more preferably not less than 15 wt %, further preferably not less than 20 wt %, particularly preferably not less than 25 wt %. It is preferably not more than 70 wt %, more preferably not more than 65 wt %, further preferably not more than 60 wt %, particularly preferably not more than 55 wt %.

The drug-containing layer composition of the percutaneous absorption formulation provided by the present invention can comprise plasticizer. The plasticizer that can be used in the present invention include, but is not limited thereto, paraffin process oil, naphthalene process oil, aromatic process oil, olive oil, *camellia* oil, tall oil, castor oil, isopropyl myristate, hexyl lauric acid, mineral oil, octyldodecylmyristate, propylene glycol. More than two of these components can be mixed to use, and the mix proportion of the styrene-isoprene-styrene block copolymer: plasticizer, considering the maintenance of the sufficient cohesiveness of the percutaneous absorption preparation, is preferably 1:0.25-1:5.0 by weight, more preferably 1:0.3-1:3.0 by weight, further preferably 1:0.4-1:2.0 by weight.

The content of the plasticizer in the drug-containing layer is preferably not less than 10 wt %, further preferably not less than 20 wt %, further preferably not less than 25 wt %, particularly preferably not less than 30 wt %. In addition, it is preferably not more than 80 wt %, more preferably not more than 75 wt %, further preferably not more than 70 wt %, particularly preferably not more than 65 wt %.

Tackifier resin can be added to the drug-containing layer to adjust the adhesiveness of the percutaneous absorption preparation of the present invention. The tackifier resin that can be used includes, but is not limited thereto, rosin derivatives, alicyclic hydrogenated saturated hydrocarbon, aliphatic hydrogenated hydrocarbon, and the present invention typically used terpene resin.

However, when a tackifier is contained in the drug-containing layer, the content of the tackifier in the drug-containing layer is preferably not more than 20 wt % to decrease skin irritation and the like. The content is preferably not more than 15 wt %, more preferably not more than 10 wt %, further preferably not more than 8 wt %, and the absence of a tackifier is most preferable. That is, in relation to the skin adhesiveness of the patch, the content of the tackifier is adjusted according to the kind, content and content ratio of donepezil, styrene-isoprene-styrene block copolymer, a solubilizer and a plasticizer. When sufficient skin adhesiveness is obtained without containing a tackifier, a tackifier is not necessary.

The percutaneous absorption preparation provided by the present invention can comprise antioxidant when necessary. The antioxidant includes, but is not limited thereto, commonly known antioxidant or its derivatives for example ascorbic acid, dibutylhydroxy toluene, butyl hydroxyanisol, cystein, glutathione, tryptophane, methionin, methanesulfonic acid, maleic acid, citric acid.

Advantageous Effects

The percutaneous absorption preparation of the present invention not only does not form the drug crystal precipitate, but also show the high degree of skin penetration and no skin irritation when attached.

Therefore, the percutaneous absorption preparation according to the present invention can be useful used as an alternative to the traditional oral preparations for treating dementia.

DESCRIPTION OF DRAWINGS

The patent or application file contains at least one drawing executed in color. Copies of this patent or patent application publication with color drawing(s) will be provided by the Office upon request and payment of the necessary fee.

FIG. 8 shows blood concentration level profile of the percutaneous absorption preparation comprising donepezil.

BEST MODE

The present invention is described in more detail hereinafter through embodiments and experimental examples. These examples do not limit the scope of the present invention and is only intended to illustrate the present invention in detail.

<Experimental Example 1> Evaluation of the Solubility of Donepezil in the Solubilizers The solubility of donepezil in the various solubilizers was evaluated.

Figure 1:
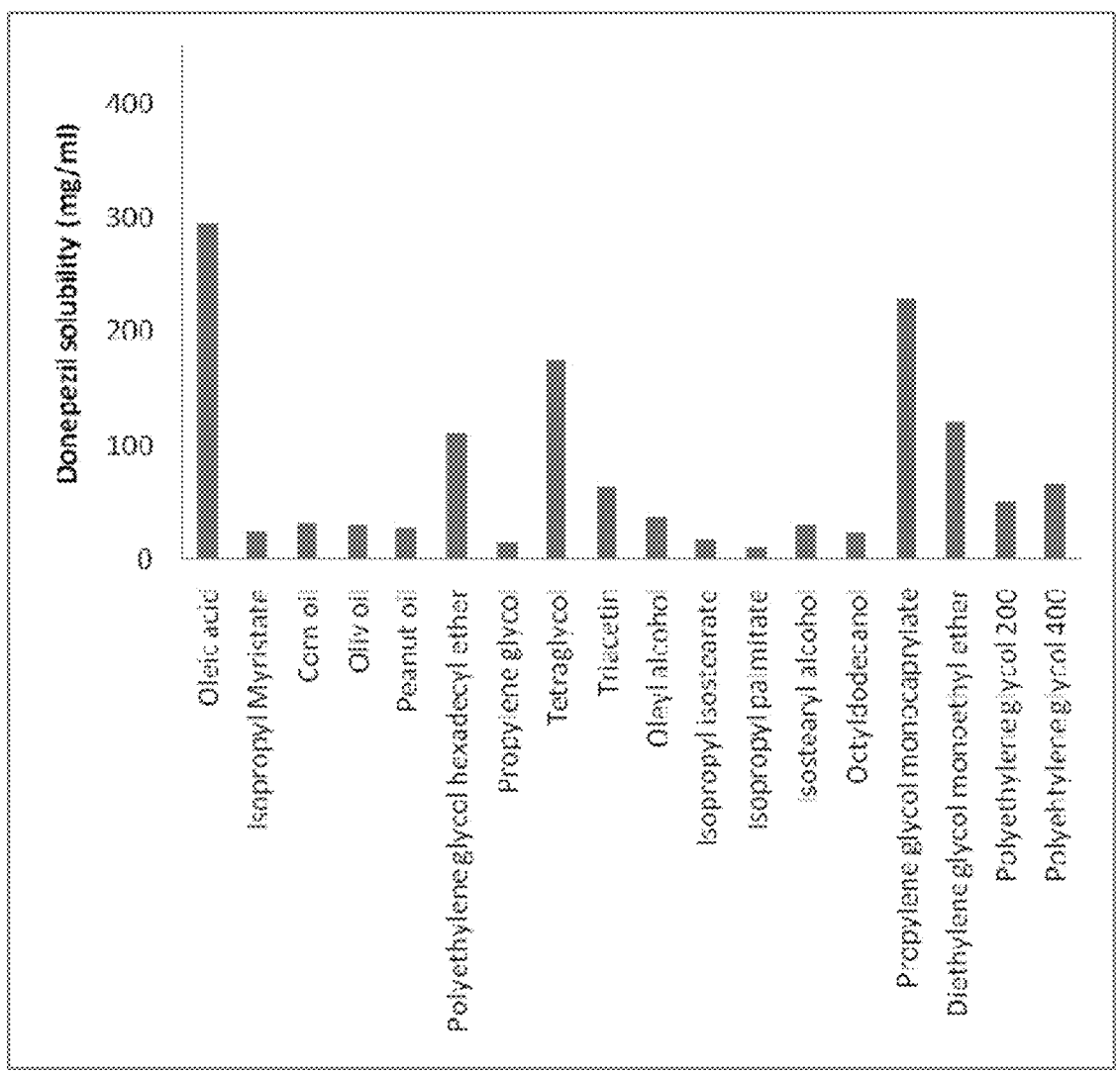
FIG. 1 shows the solubility of donepezil in various solubilizers.

The solubility was evaluated by adding a large excess of donepezil in 5 mL of each solubilizer, maintaining them for 24 hours in a 25° C. constant-temperature shaking water bath, and filtered the supernatant through 0.45 um filter. The filtrate was used to calculate the solubility of donepezil by liquid chromatography. The solubility is shown in FIG. 1.
<High Performance Liquid Chromatography Conditions>
Column: Capcellpak C18, 4.6×150 mm, 5 um
Mobile phase: 2.5 g of sodium decanesulfonate was dissolved in 650 mL of water. Then 1 mL of 70% perchloric acid and 350 mL of acetonitrile solution were added to the solution. The solution was filtered and bubbles within were removed using an ultrasonic washing machine. The resulting solution was used as the mobile phase.
Column temperature: 35° C.
Flow rate: 1.4 mL/min
Injection volume: 20 uL
Ultraviolet wavelength: 271 nm
As shown in FIG. 1, the solubility evaluation shows that the solubility of donepezil was the highest in oleic acid. Nine solubilizers that donepezil showed high solubility in, based on the solubility evaluation, were used to make the percutaneous absorption preparations comprising donepezil of the below embodiments and comparative examples.

<Embodiment 1> Formulation of the Percutaneous Absorption Preparation According to the Present Invention (1)

4.5 g of propylene glycol monocaprylate, 5.2 g of styrene-isoprene-styrene block copolymer, 8.2 g of octyldodecyl myristate, and 4.5 g of propylene glycol monocaprylate were dissolved in 15 g of ethylacetate and then added to 1 g of donepezil and dissolved thoroughly, like the composition disclosed in the table 1 below. The percutaneous absorption preparation was formulated by spreading the resulting solution on the silicon coated PET film and then drying it for 30 minutes in 80° C. oven and attaching it to backing film.

<Embodiment 2> Formulation of the Percutaneous Absorption Preparation According to the Present Invention (2)

To test the degree of skin penetration and crystal precipitation contingent upon the terpene resin, the percutaneous absorption preparation was formulated with the components disclosed in table 1 below through the same process as the embodiment 1 above.

TABLE 1

| Category | Ingredient (g) | Embodiment 1 | Embodiment 2 |
|---|---|---|---|
| Active component | Donepezil | 1 | 1 |
| Base polymer for adhesive | Styrene-isoprene-styrene block copolymer | 5.2 | 5.2 |
| Tackifier | Terpene resin | — | 1.3 |
| Solubilizer | Propylene glycol monocaprylate | 4.5 | 4.5 |
| Solubilizer | Octyldodecyl myristate | 8.2 | 8.2 |
| | Total | 18.9 | 20.2 |

<Embodiment 3 and 4> Formulation of the Percutaneous Absorption Preparation According to the Present Invention (3)

With the components disclosed in table 2 below, the percutaneous absorption preparations of embodiment 3, with the same components as the embodiment 1 but in different amounts, and embodiment 4, with different plasticizer from embodiment 1, were formulated through the same process as the embodiment 1 above.

TABLE 2

| Category | Ingredient (g) | Embodiment 3 | Embodiment 4 |
|---|---|---|---|
| Active component | Donepezil | 1 | 1 |
| Base polymer for adhesive | Styrene-isoprene-styrene block copolymer | 12 | 12 |
| Solubilizer | Propylene glycol monocaprylate | 3 | 3 |
| Plasticizer | Octyldodecyl myristate | 6 | — |
| | Mineral oil | — | 6 |
| | Total | 22 | 22 |

<Embodiment 5> Formulation of the Percutaneous Absorption Preparation with Various Amounts of Solubilizer According to the Present Invention (4)

To select the optimum ratio of donepezil to propylene glycol monocaprylate of the present invention, the amounts of solubilizer of the percutaneous absorption preparations of embodiment 5-1 through 5-3 were changed to differ from that of embodiment 2 and were formulated with components disclosed in table 3 below through the same process as embodiment 2.

TABLE 3

| Category | Ingredient (g) | Embodiment 5-1 | Embodiment 5-2 | Embodiment 5-3 |
|---|---|---|---|---|
| Active component | Donepezil | 1.0 | 1.0 | 1.0 |
| Base polymer for adhesive | Styrene-isoprene-styrene block copolymer | 5.2 | 5.2 | 5.2 |
| Tackifier | Terpene resin | 1.3 | 1.3 | 1.3 |
| Solubilizer | Propylene glycol monocaprylate | 4.5 | 3 | 1.5 |
| Plasticizer | Octyldodecyl myristate | 8.2 | 8.2 | 8.2 |
| | Total | 20.2 | 18.7 | 17.2 |

<Embodiment 6> Formulation of the Percutaneous Absorption Preparation with Various Amounts of Adhesive According to the Present Invention (5)

To select the optimum ratio of styrene-isoprene-styrene block copolymer of the present invention, the amounts of base polymer for adhesive of the percutaneous absorption preparations of embodiment 6-1 through 6-6 were changed to differ from that of embodiment 2 and were formulated with components disclosed in table 4 below through the same process as embodiment 2.

TABLE 4

(unit: g)

| Category | Ingredient (wt %) | Embodiment 6-1 | Embodiment 6-2 | Embodiment 6-3 | Embodiment 6-4 | Embodiment 6-5 | Embodiment 6-6 |
|---|---|---|---|---|---|---|---|
| Active component | Donepezil | 1 (5.3%) | 1 (4.9%) | 1 (4.5%) | 1 (4.0%) | 1 (3.6%) | 1 (2.5%) |
| Base polymer for adhesive | Styrene-isoprene-styrene block copolymer | 3 (15.8%) | 4.5 (22.0%) | 6 (27.3%) | 9 (36.0%) | 12 (42.9%) | 24 (60.0%) |
| Tackifier | Terpene resin | 3 (15.8%) | 3 (14.6%) | 3 (13.6%) | 3 (12.0%) | 3 (10.7%) | 3 (7.5%) |
| Solubilizer | Propylene glycol monocaprylate | 3 (15.8%) | 3 (14.6%) | 3 (13.6%) | 3 (12.0%) | 3 (10.7%) | 3 (7.5%) |
| Plasticizer | Octyldodecyl myristate | 9 (47.3%) | 9 (43.9%) | 9 (41.0%) | 9 (36.0%) | 9 (32.1%) | 9 (22.5%) |
| | Total | 19 (100%) | 20.5 (100%) | 22 (100%) | 25 (100%) | 28 (100%) | 40 (100%) |

<Comparative Example 1 Through 9> Formulation of the Percutaneous Absorption Preparation Comprising Donepezil with Different Solubilizers Based on the evaluation of solubility in experimental example 1, eight solubilizers that donepezil showed high solubility in were selected. Comparative example 1 through 8 were formulated with components disclosed in table 5 below through the same process as embodiment 2, comprising each of the solubilizers mentioned above and the same components of embodiment 2, except for the solubilizer. Comparative example 9 was formulated without a solubilizer.

TABLE 5

(unit: g)

| | Ingredient | Comparative example 1 | 2 | 3 | 4 | 5 | 6 | 7 | 8 | 9 |
|---|---|---|---|---|---|---|---|---|---|---|
| | Donepezil | 1 | 1 | 1 | 1 | 1 | 1 | 1 | 1 | 1 |
| | Styrene-isoprene-styrene block copolymer | 5.2 | 5.2 | 5.2 | 5.2 | 5.2 | 5.2 | 5.2 | 5.2 | 5.2 |
| | Terpene resin | 1.3 | 1.3 | 1.3 | 1.3 | 1.3 | 1.3 | 1.3 | 1.3 | 1.3 |
| Solubilizer | Polyethylene glycol hexadecyl ester | 4.5 | | | | | | | | |

TABLE 5-continued (unit: g)

| Ingredient | Comparative example | | | | | | | | |
|---|---|---|---|---|---|---|---|---|---|
| | 1 | 2 | 3 | 4 | 5 | 6 | 7 | 8 | 9 |
| Tetraglycol | 4.5 | | | | | | | | |
| Triacetin | | 4.5 | | | | | | | |
| Diethylene glycol monoethyl ether | | | 4.5 | | | | | | |
| Polyethylene glycol 400 | | | | 4.5 | | | | | |
| Polyethylene glycol 200 | | | | | 4.5 | | | | |
| oleyl alcohol | | | | | | | 4.5 | | |
| oleic acid | | | | | | | | 4.5 | |
| Octyldodecyl myristate | 8.2 | 8.2 | 8.2 | 8.2 | 8.2 | 8.2 | 8.2 | 8.2 | 8.2 |
| Total | 20.2 | 20.2 | 20.2 | 20.2 | 20.2 | 20.2 | 20.2 | 20.2 | 15.7 |

<Comparative Example 10 Through 12> Formulation of the Percutaneous Absorption Preparation Comprising Donepezil with Different Adhesives Comparative examples 10 through 12 were formulated with components disclosed in table 6 below through the same process as embodiment 1, comprising different adhesives from embodiment 1. Comparative example 10 through 12 each used polyethylene vinyl acetate (containing 40% vinyl acetate), an EVA adhesive, acrylic adhesive Duro-Tak® 87-9301, and polyisobutylene adhesive, respectively. When polyisobutylene was used as a base polymer for adhesive, hexane was used as an organic solvent.

TABLE 6

| | Ingredient (g) | Comparative example 10 | Comparative example 11 | Comparative example 12 |
|---|---|---|---|---|
| Active component | Donepezil | 1 | 1 | 1 |
| Adhesive | Polyethylene vinyl acetate | 12 | — | — |
| | Duro-Tak ® 87-9301 | — | 12 | — |
| | Polyisobutylene | — | — | 12 |
| Solubilizer | Propylene glycol monocaprylate | 3 | 3 | 3 |
| Plasticizer | Octyldodecyl myristate | 6 | 6 | 6 |
| | Total | 22 | 22 | 22 |

<Comparative Example 13> Formulation of the Percutaneous Absorption Preparation Comprising Donepezil To select the optimum ratio of donepezil to propylene glycol monocaprylate of the present invention, the amounts of solubilizer of the percutaneous absorption preparations of comparative example 13 were changed to differ from that of embodiment 2 and were formulated with components disclosed in table 7 below through the same process as embodiment 2.

TABLE 7

| Category | Ingredient (g) | Comparative example 13 |
|---|---|---|
| Active component | Donepezil | 1.0 |
| Base polymer for adhesive | Styrene-isoprene-styrene block copolymer | 5.2 |
| Tackifier | Terpene resin | 1.3 |
| Solubilizer | Propylene glycol monocaprylate | 0.75 |
| Plasticizer | Octyldodecyl myristate | 8.2 |
| | Total | 16.45 |

<Experimental Example 2> Evaluation of the Degree of Skin Penetration Using Hairless Rat's Skin The in-vitro permeability of the percutaneous absorption preparations prepared in examples 1 to 6 and comparative examples 1 to 13 was evaluated by using a Franz diffusion cell. The receptor chamber was filled with physiological saline containing 10% ethanol and 0.02% sodium azide as a receptor solution, and the temperature was maintained at 32±0.5° C. Each of the percutaneous absorption preparations prepared in Examples 1 to 6 and Comparative Examples 1 to 13 was cut and applied to the donor cell size using a hairless rat skin. The penetrated amount of donepezil in the receptor solution was measured over time using liquid chromatography. FIG. 2 through 6 shows patterns of drug release over time of patches made in embodiment 1 through 6 and comparative example 1 through 13.

Figure 2:
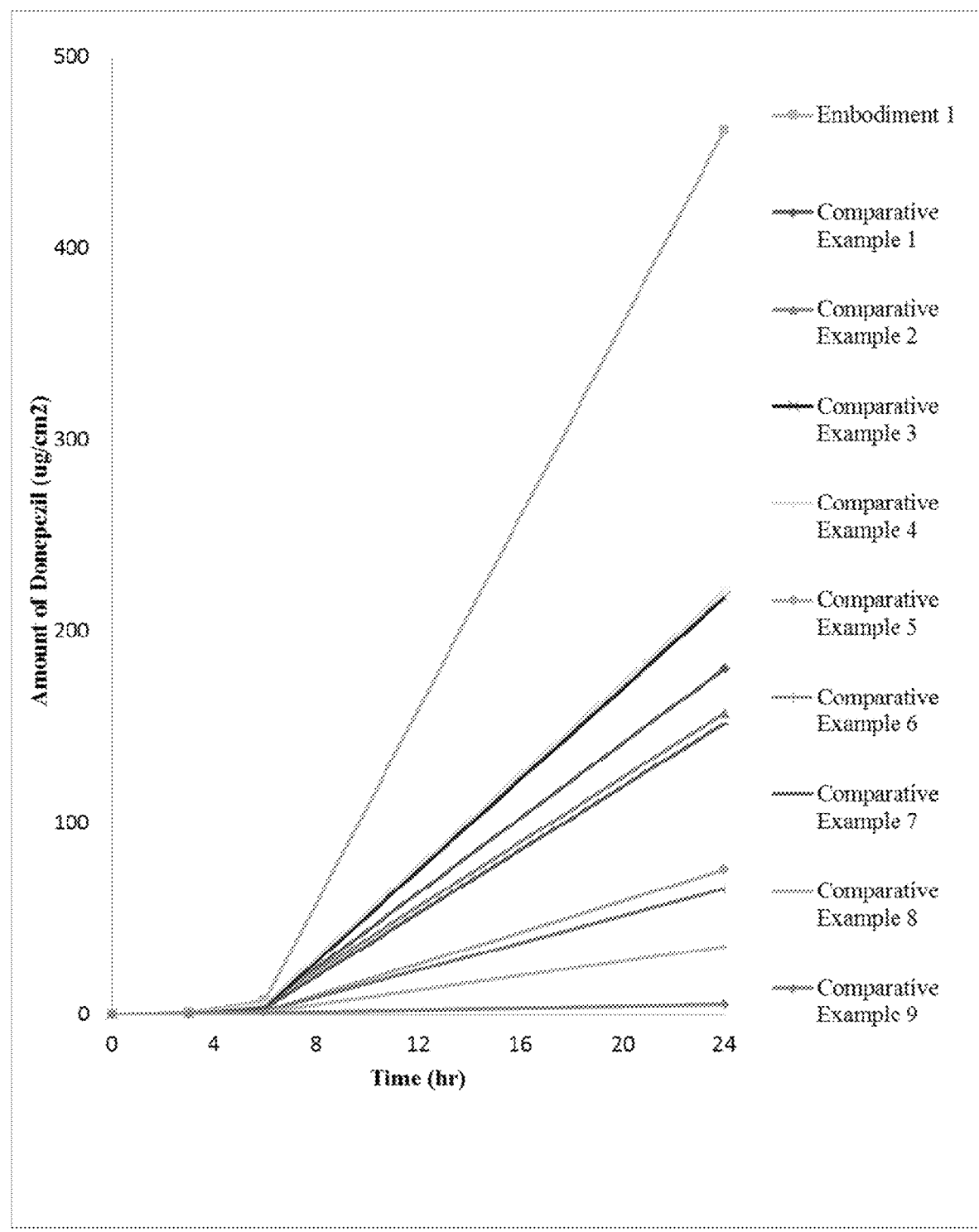
FIG. 2 shows the degree of skin penetration according to various solubilizers.

(1) Evaluation of the Degree of Skin Penetration According to Various Absorption Enhancers As shown in FIG. 2, comparative example 9 without solubilizer induce little penetration of donepezil. Also, oleic acid (comparative example 8), which showed high solubility of donepezil, also showed very low level of penetration. However it can be seen that embodiment with propylene glycol monocaprylate as the solubilizer showed significant increase of degree of skin penetration. This shows the degree of skin penetration of propylene glycol monocaprylate is great.

(2) Evaluation of the Degree of Skin Penetration with/without Terpene Resin

Figure 3:
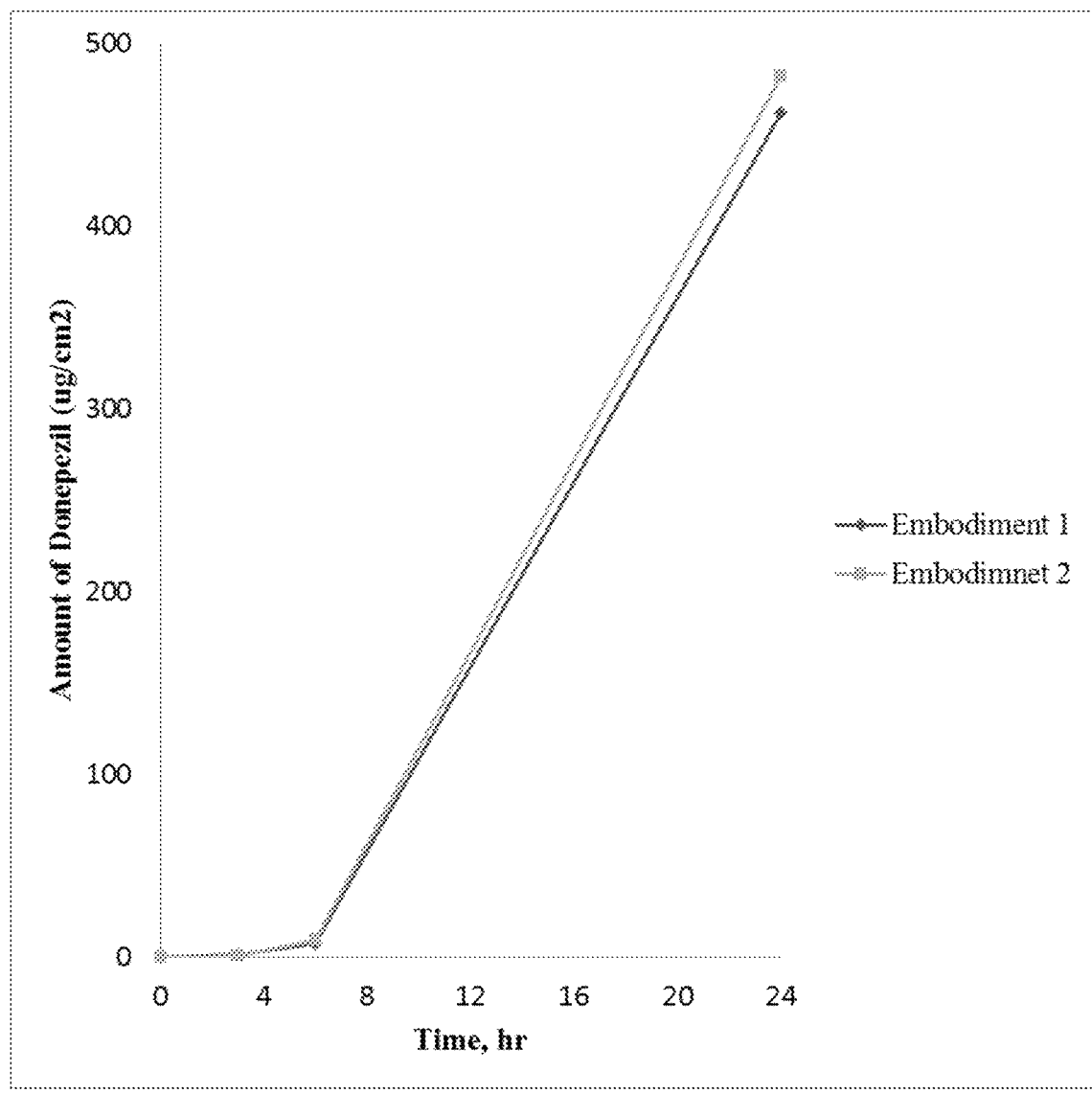
FIG. 3 shows the degree of skin penetration with/without terpene resin.

As shown in FIG. 3, embodiment 1 with terpene resin and embodiment 2 without terpene resin showed no difference in the degree of skin penetration.

drug crystal precipitation. The appearance of crystal precipitation was observed with microscopes for crystal formations after storing the percutaneous absorption preparations according to embodiment 1 through 6 under 25° C. 60% RH for 1 month. Table 8 below shows the results.

TABLE 8

| | Embodiment 1 | Embodiment 2 | Embodiment 3 | Embodiment 4 | Embodiment 5-1 | Embodiment 5-2 | Embodiment 5-3 | Embodiment 6-2 | Embodiment 6-3 | Embodiment 6-4 | Embodiment 6-5 | Embodiment 6-6 |
|---|---|---|---|---|---|---|---|---|---|---|---|---|
| Crystal precipitation | X (No) | X (No) | X (No) | X (No) | X (No) | X (No) | X (No) | X (No) | X (No) | X (No) | X (No) | X (No) |

Figure 4:
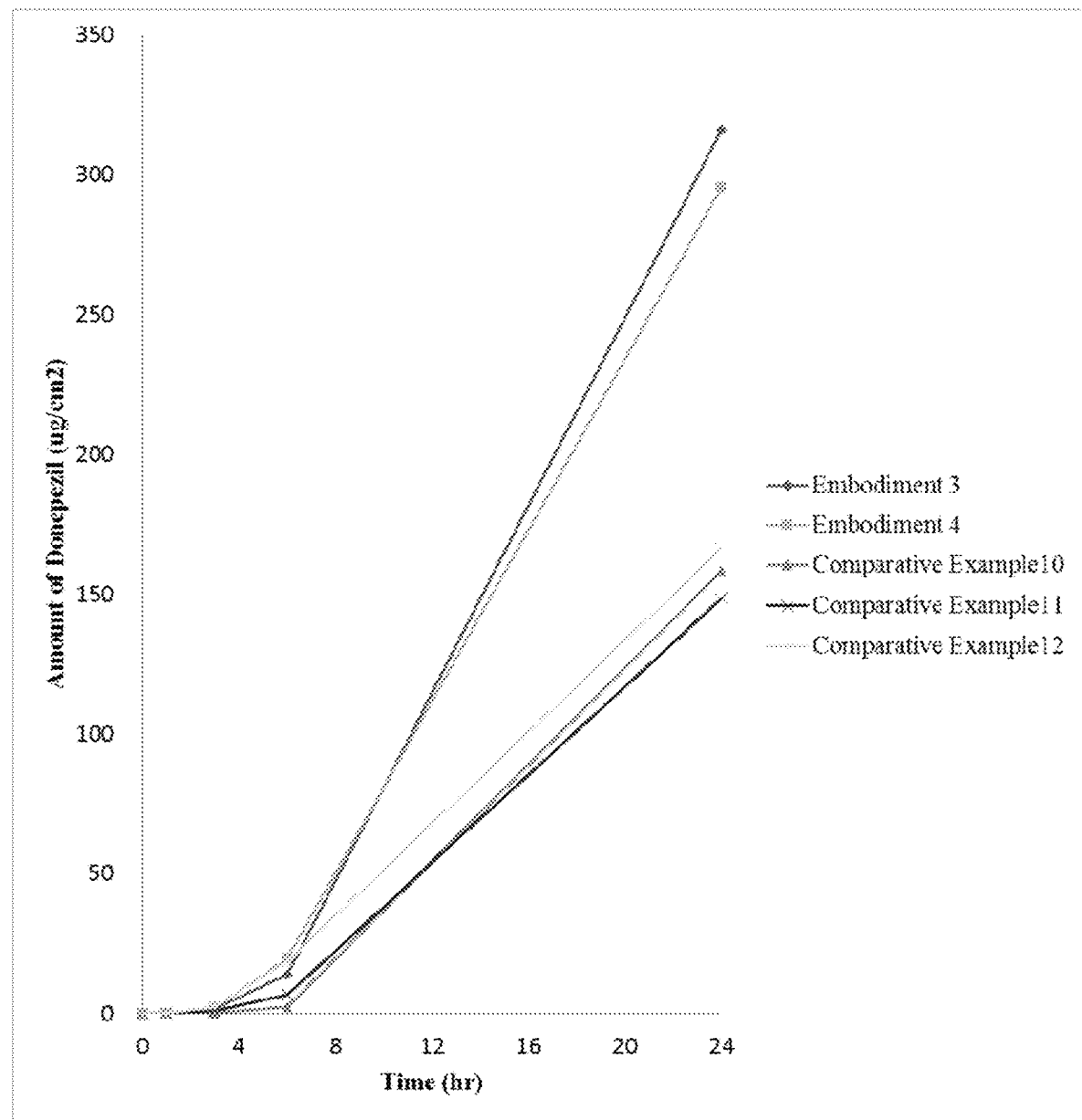
FIG. 4 shows the degree of skin penetration according to various plasticizers and adhesives.

(3) Evaluation of the Degree of Skin Penetration Contingent Upon Change of Plasticizer and Adhesive As shown in FIG. 4, embodiment 3 through 4, wherein octyldodecyl myristate is changed to mineral oil as the plasticizer, showed no change in the degree of skin penetration. On the contrary, comparative example 10 through 12, wherein adhesive is changed, showed significant decrease in the degree of skin penetration compared to when styrene-isoprene-styrene block copolymer is used as the base polymer for adhesive.

Figure 5:
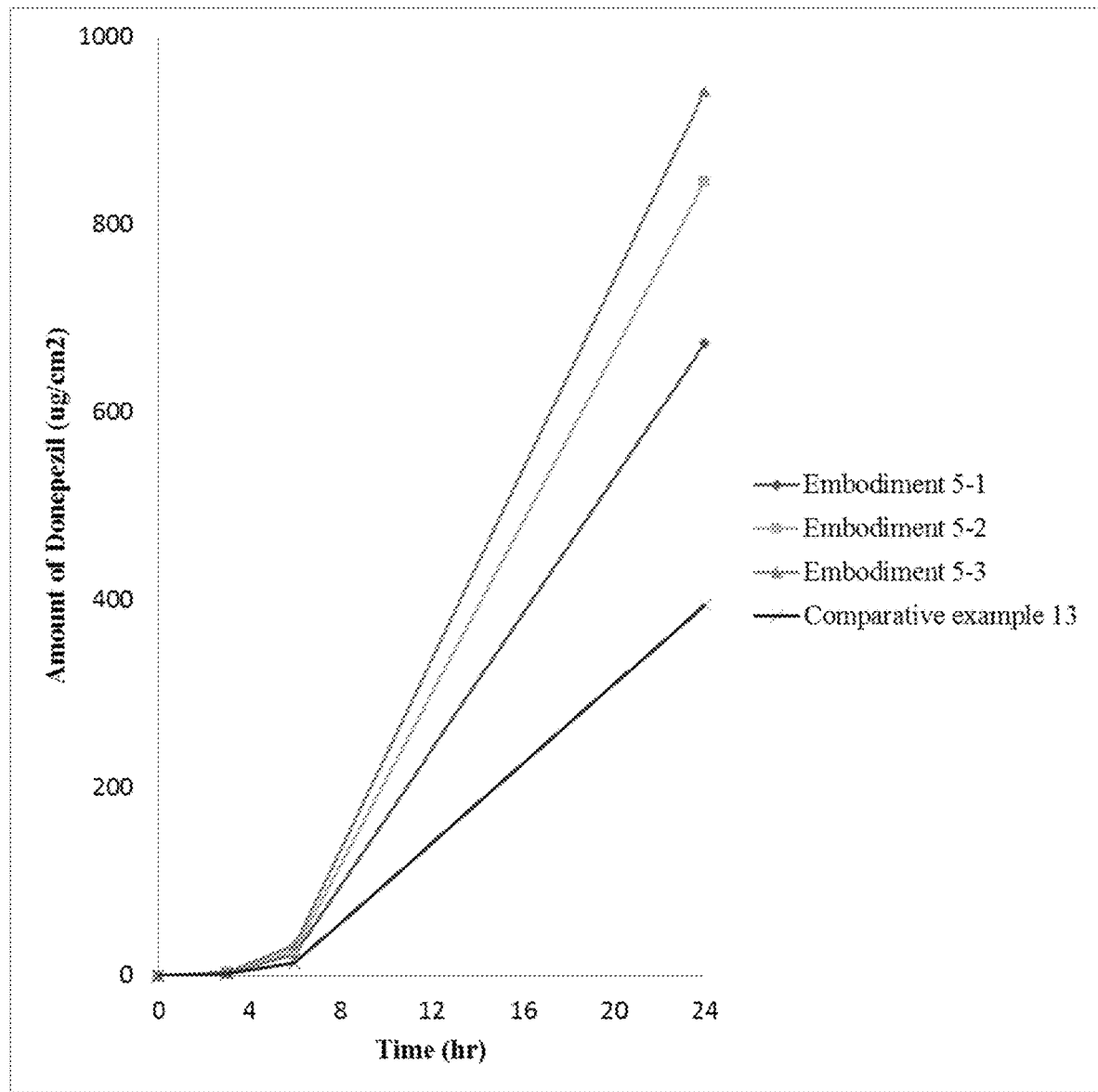
FIG. 5 shows the degree of skin penetration according to the ratio of donepezil and propylene glycol monocaprylate.
Figure 6:
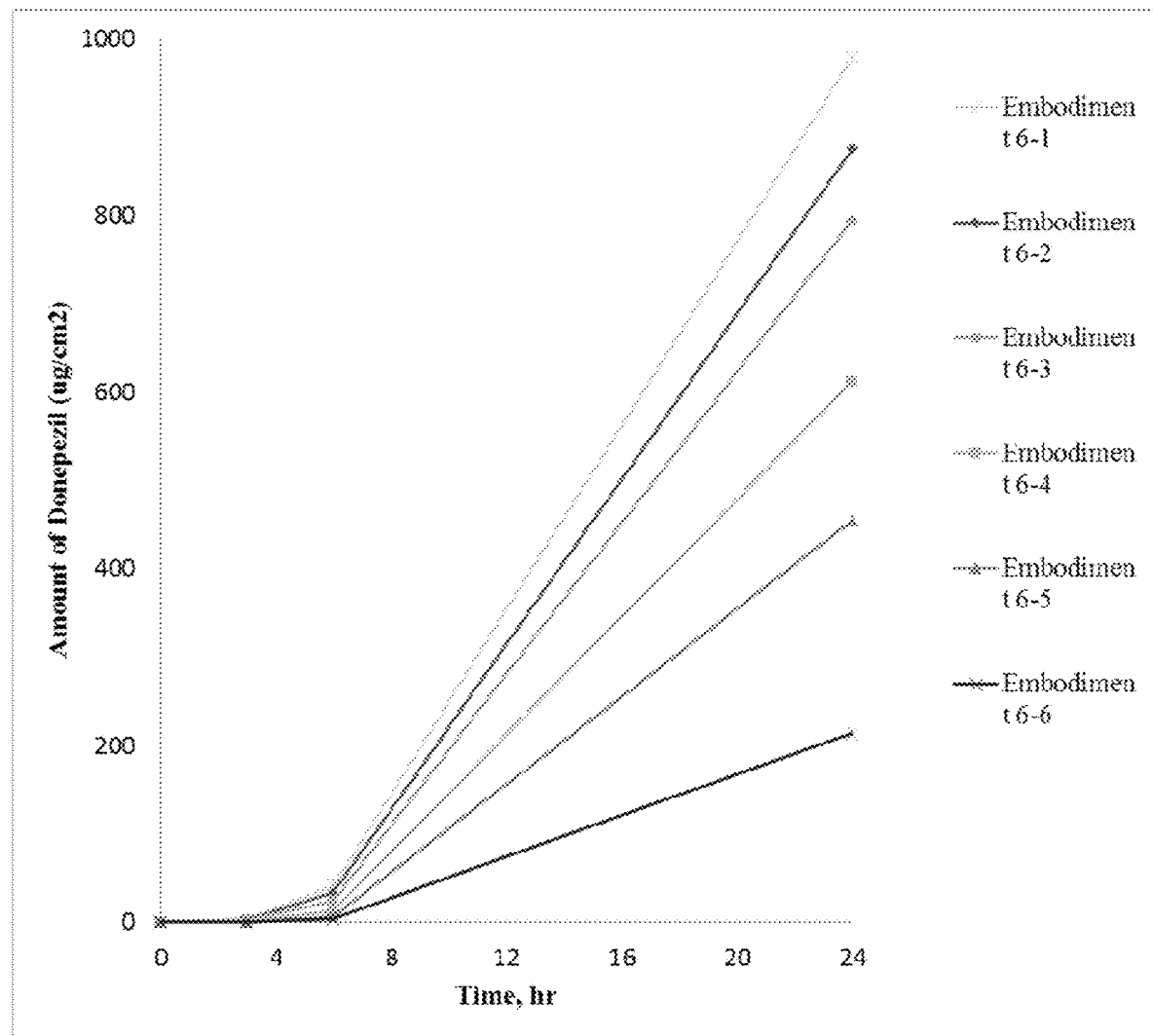
FIG. 6 shows the degree of skin penetration according to the ratio of styrene-isoprene-styrene block copolymer

(4) Evaluation of the Degree of Skin Penetration According to the Ratio of Donepezil to Propylene Glycol Monocaprylate The percutaneous absorption preparation formulated according to embodiment 5 and comparative example 13 was evaluated using experimental franz diffusion cell. The results show that when the ratio is below 1:0.75 (comparative example 13) drug precipitates formed thereby significantly decreasing the degree of skin penetration, and that when the ratio is between 1:1.5 and 1:4.5, the degree of skin penetration was great without drug crystal precipitation (FIG. 5).

(5) Evaluation of the Degree of Skin Penetration According to the Ratio of Styrene-Isoprene-Styrene Block Copolymer To determine the optimum ratio of styrene-isoprene-styrene block copolymer in the drug-containing layer, the percutaneous absorption preparation prepared according to Example 6 was evaluated using a franz diffusion cell.

As a result, skin permeability tended to decrease as the weight % of styrene-isoprene-styrene block copolymer for adhesive in the drug-containing layer was increased. On the other hand, as the weight % of the styrene-isoprene-styrene block copolymer in the drug-containing layer decreased, the gel cohesion of the drug-containing layer became weaker. In Example 6-1, the gel cohesive force weakened and the part of the drug-containing layer remained on the surface of the skin when the percutaneous absorption preparation was removed after skin permeability study. Based on the results, for the styrene-isoprene-styrene block copolymer in the drug-containing layer to have sufficient gel cohesion and skin permeability, the amount of the styrene-isoprene-styrene block copolymer in the drug-containing layer needed is 10 wt % to 70 wt %, more preferably 20 wt % to 60% by weight.

<Experimental Example 3> Evaluation of Drug Crystal Precipitation

The percutaneous absorption preparations according to embodiment 1 through 6 were evaluated for the presence of As shown in table 8, when donepezil:propylene glycol monocaprylate used is 1:1.5, it was found that crystal precipitates do not form because of high solubility of donepezil in propylene glycol monocaprylate. Also, embodiment 1 and 2 showed no appearance of crystal precipitates irrespectively to the addition of terpene resin.

<Experimental Example 4> Evaluation of Skin Irritation

The degree of skin irritation of the percutaneous absorption preparation according to the present invention was evaluated. Marketed product Exelon 5 mg patch was used as comparative example for the above evaluation of the percutaneous absorption preparation according to embodiment 6-5 of the present invention.

Four shaved, white rabbits were used for the evaluation. Embodiment 6-5 and marketed preparation Exelon were cut to 5 cm². They were attached for 24 hours before being detached. The red spots and edema formation on the attachment area of the percutaneous absorption preparation after 24 hours and 74 hours were observed with bare eyes and evaluated with method disclosed in table 9. The results are shown in table 10 and FIG. 7.

TABLE 9

| Red spots and incrustation | Point(s) | Edema formation | Point(s) |
|---|---|---|---|
| No red spot | 0 | No edema | 0 |
| Very light red spot (barely distinguished with bare eyes) | 1 | Very light edema (barely distinguished with bare eyes) | 1 |
| Clear red spot | 2 | Light edema (clearly swollen that the edges can be clearly distinguished) | 2 |
| Slightly severe red spot | 3 | Average edema (swollen to approx. 1 mm) | 3 |
| Severe red spot (red flare) and light incrustation | 4 | Severe edema (swollen more than 1 mm and extended beyond the attached area) | 4 |
| Severest | 4 | Severest | 4 |

TABLE 10

| Category | Skin reaction | Observation period | Individual 1 | Individual 2 | Individual 3 | Individual 4 | Average |
|---|---|---|---|---|---|---|---|
| Embodiment 6-5 | Red spot | 24 hr | 1 | 1 | 0 | 1 | 0.75 |
| | | 72 hr | 1 | 1 | 1 | 0 | 0.75 |
| | Edema | 24 hr | 0 | 0 | 0 | 0 | 0 |
| | | 72 hr | 0 | 0 | 0 | 0 | 0 |
| Exelon patch | Red spot | 24 hr | 3 | 3 | 2 | 2 | 2.5 |
| | | 72 hr | 3 | 2 | 2 | 1 | 2 |
| | Edema | 24 hr | 0 | 0 | 0 | 0 | 0 |
| | | 72 hr | 0 | 0 | 0 | 0 | 0 |

Figure 7:
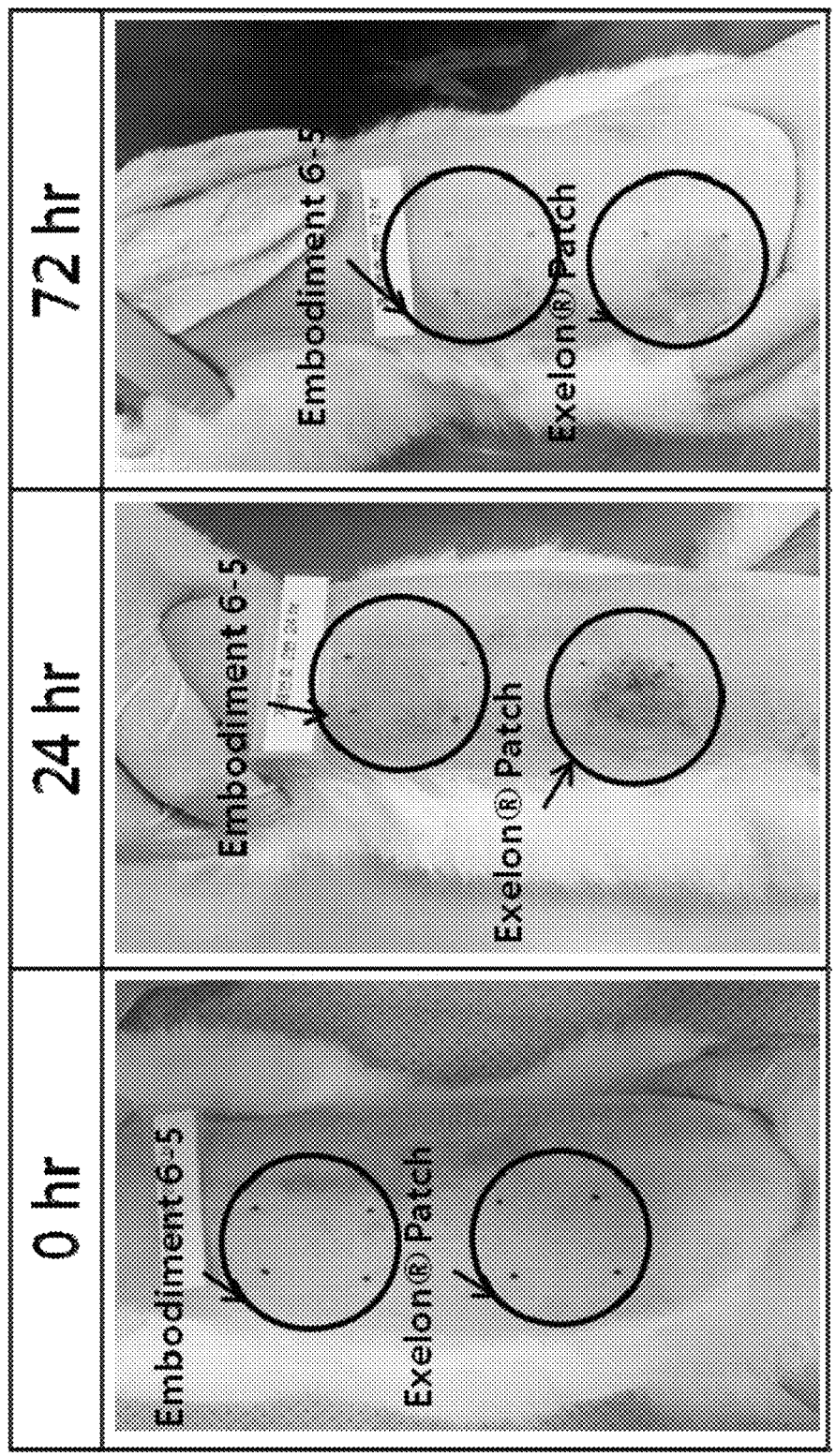
FIG. 7 shows test results of skin irritation evaluation.

As shown in table 10 and FIG. 7, embodiment 6-5 of the present invention induced no edema and induced light red spot with 0.75 point, whereas, marketed Exelon® patch induced no edema but induced 2.5 (24 hr) and 2.0 (74 hr) of severe red spot.

This shows that the percutaneous absorption preparation comprising donepezil of the present invention induces significantly low degree of skin irritation compared to the market Exelon®.

<Experimental Example 5> Evaluation of Rat PK

The pharmacokinetics of the percutaneous absorption preparations according to embodiment 1 and 6-5 of the present invention were evaluated using hairless rat and the results are shown in table 11. For comparison, comparative example 3 (triacetin as the solubilizer), with the highest degree of skin penetration based on the in-vitro evaluation of the degree of skin penetration of the comparative examples, and oral preparation of reference example 1 (oral composition comprising 5 mg donepezil) were evaluated as well.

Embodiment 1 and comparative example 3, which comprise the same component except for the solubilizers, were cut into 2.5 cm². Embodiment 6-5 was cut into 4 cm² and 8 cm². They were attached to hairless rats for 7 days before being detached. Blood was drawn 0, 4, 8, 24, 30, 48, 72, 96, 144, 168 hours after patch attachment and the blood level of donepezil was measured. In reference example 1, donepezil was dissolved at 2.5 mg/mL in distilled water, and 2 mL of the donepezil solution was orally administered. The blood was drawn 0, 0.5, 1, 2, 4, 6, 24 hours later and the amount of donepezil in blood was measured.

TABLE 11

| | Embodiment 1 (2.5 cm²) | Embodiment 6-5 (4 cm²) | Embodiment 6-5 (8 cm²) | Comparative example 3 | Reference example 1 |
|---|---|---|---|---|---|
| Content of drug in patch (mg/sheet) | 4 | 5 | 10 | 4 | 5 |
| Residual amount of drug after 7 days of attachment (%) | 6.6 | 9.5 | 15.3 | 34.6 | — |
| Degree of skin penetration (%) | 93.4 | 90.5 | 84.7 | 65.4 | — |
| $AUC_{inf}$ (ng * hr/mL) | 3241.2 | 3913.9 | 8439.4 | 2308.0 | 1167.4 |
| Cmax (ng/mL) | 97.1 | 109.8 | 228.1 | 49.7 | 95.8 |
| Tmax (hr) | 24 | 24 | 24 | 24 | 2 |

As shown in table 11 above, the residual amount of drug in patch after 7 days of attachment of embodiment 1 of the present invention was 6.6%, indicating 93.4% of the drug penetrated the skin, whereas, the residual amount of drug in patch after 7 days of attachment of comparative example 3 was 34.6% and thereby only 65.4% of the drug penetrated the skin.

The results of the in-vivo evaluation of the degree of skin penetration of the above experimental example 6 conform with the results of in-vitro evaluation of the degree of skin penetration of the above experimental example 2 (1). This shows that the percutaneous absorption preparation comprising propylene glycol monocaprylate as the solubilizer according to the present invention induce great degree of drug penetration.

Also, the evaluation of blood level of donepezil of embodiment 6-5 with patch area of 4 cm² and 8 cm² shows that the blood concentration level proportionally increases as the area of the percutaneous absorption preparation increases. Particularly when embodiment 6-5 in 4 cm² and oral administration of reference example 1 with 5 mg donepezil are compared, AUC of percutaneous administration increased approximately 335% to 3913.9 ng*hr/ml compared to 1167.4 ng*hr/ml of the oral administration. This shows that the percutaneous absorption preparation according to the present invention can achieve significantly higher blood concentration level compared to the oral administration with the same drug dosage.

The invention claimed is:

1. A percutaneous absorption preparation for the treatment of dementia comprising a backing layer, a drug-containing layer, and a release liner,
   wherein the drug-containing layer of the percutaneous absorption preparation comprises (a) donepezil or a pharmaceutically acceptable salt thereof as an active component, (b) a propylene glycol monocaprylate as a solubilizer, (c) a styrene-isoprene-styrene block copolymer as an adhesive, and (d) a plasticizer,
   wherein a ratio of donepezil or the pharmaceutically acceptable salt thereof: the propylene glycol monocaprylate is not less than 1:1.5 by weight,
   wherein the styrene-isoprene-styrene block copolymer makes up 10-70 wt % of a total weight of the drug-containing layer, and
   wherein the plasticizer (d) is selected from the group consisting of paraffin process oil, naphthalene process oil, aromatic process oil, olive oil, camellia oil, tall oil, castor oil, isopropyl myristate, hexyl lauric acid, mineral oil, octyldodecyl myristate, propylene glycol, and a combination thereof.

2. The percutaneous absorption preparation according to claim 1, wherein the donepezil as an active component is donepezil free base.

3. The percutaneous absorption preparation according to claim 1, wherein the propylene glycol monocaprylate makes up 1-40 wt % of the total weight of the drug-containing layer.

4. The percutaneous absorption preparation according to claim 3, wherein the propylene glycol monocaprylate makes up 3-30 wt % of the total weight of the drug-containing layer.

5. The percutaneous absorption preparation according to claim 4, wherein the propylene glycol monocaprylate makes up 5-25 wt % of the total weight of the drug-containing layer.

6. A process for preparing the percutaneous absorption preparation of claim 1, wherein the process comprises the following steps:
 (a) dissolving propylene glycol monocaprylate, styrene-isoprene-styrene block copolymer and doenpezil free base in an organic solvent;
 (b) casting the solution obtained in step (a) on a release linear, followed by drying, to form a drug-containing layer; and
 (c) laminating the drug-containing layer with a backing layer.

7. The percutaneous absorption preparation according to claim 1, wherein the ratio of donepezil or the pharmaceutically acceptable salt thereof: the propylene glycol monocaprylate is 1:1.5-1:4.5 by weight.

* * * * *